US009280065B2

(12) United States Patent
Van De Kerkhof

(10) Patent No.: US 9,280,065 B2
(45) Date of Patent: Mar. 8, 2016

(54) INSPECTION APPARATUS TO DETECT A TARGET LOCATED WITHIN A PATTERN FOR LITHOGRAPHY

(71) Applicant: ASML Netherlands B.V., Veldhoven (NL)

(72) Inventor: Marcus Adrianus Van De Kerkhof, Helmond (NL)

(73) Assignee: ASML Netherlands B.V., Veldhoven (NL)

(*) Notice: Subject to any disclaimer, the term of this patent is extended or adjusted under 35 U.S.C. 154(b) by 0 days.

(21) Appl. No.: 14/664,007

(22) Filed: Mar. 20, 2015

(65) Prior Publication Data

US 2015/0192858 A1 Jul. 9, 2015

Related U.S. Application Data

(63) Continuation of application No. 12/989,902, filed as application No. PCT/EP2009/003051 on Apr. 27, 2009, now Pat. No. 8,988,658.

(60) Provisional application No. 61/071,673, filed on May 12, 2008.

(51) Int. Cl.
*G03F 7/20* (2006.01)
*G01N 21/21* (2006.01)
(Continued)

(52) U.S. Cl.
CPC .......... *G03F 7/70633* (2013.01); *G01N 21/211* (2013.01); *G03F 7/70616* (2013.01); *G01N 21/9501* (2013.01); *G01N 21/956* (2013.01);
(Continued)

(58) Field of Classification Search
CPC ............ G03F 7/70633; G03F 7/70616; G01N 21/211; G01N 21/9501; G01N 21/956
See application file for complete search history.

(56) References Cited

U.S. PATENT DOCUMENTS 6,650,422 B2 11/2003 Singh et al.
7,643,666 B2 1/2010 Setija et al.
(Continued)

FOREIGN PATENT DOCUMENTS

EP 1 628 164 A2 2/2006
EP 1 736 759 A1 12/2006
(Continued)

OTHER PUBLICATIONS

International Search Report directed to related International Patent Application No. PCT/EP2009/003051, mailed Jul. 22, 2015, from the European Patent Office, 3 pages.
(Continued)

*Primary Examiner* — Peter B Kim
*Assistant Examiner* — Michelle Iacoletti
(74) *Attorney, Agent, or Firm* — Sterne, Kessler, Goldstein & Fox P.L.L.C.

(57) ABSTRACT

A system detects targets located within patterns. It operates in the pupil plane by filtering the received signal from the surrounding pattern. A method includes illuminating a target and a surrounding pattern with radiation, detecting the radiation reflected by the target and the surrounding pattern and forming a first set of data based on the detected radiation, removing portions of the first set of data which correspond to the target to form reduced data, interpolating the remaining portions of the reduced data over the removed portions to form product data, and subtracting the product data from the first set of data to form target data.

18 Claims, 4 Drawing Sheets

(51) Int. Cl.
*G01N 21/95* (2006.01)
*G01N 21/956* (2006.01)

(52) U.S. Cl.
CPC .. *G01N 2201/06113* (2013.01); *G01N 2201/10* (2013.01)

(56) References Cited

U.S. PATENT DOCUMENTS

| | | | |
|---|---|---|---|
| 7,791,727 | B2 | 9/2010 | Den Boef et al. |
| 8,988,658 | B2 | 3/2015 | Van De Kerkhof |
| 2003/0002043 | A1 | 1/2003 | Abdulhalim et al. |
| 2003/0002590 | A1 | 1/2003 | Kaku et al. |
| 2004/0233439 | A1 | 11/2004 | Mieher et al. |
| 2009/0316979 | A1 | 12/2009 | Gidon |
| 2011/0164228 | A1 | 7/2011 | Van De Kerkhof |

FOREIGN PATENT DOCUMENTS

| | | |
|---|---|---|
| JP | 2001-343324 A | 12/2001 |
| JP | 2005-509132 A | 4/2005 |
| JP | 2006-060214 A | 3/2006 |
| JP | 2008-042202 A | 2/2008 |
| JP | 2009-545734 A | 12/2009 |
| WO | WO 2008/015230 A1 | 2/2008 |

OTHER PUBLICATIONS

International Preliminary Report on Patentability and Written Opinion directed to related International Patent Application No. PCT/EP2009/003051, mailed Nov. 25, 2010 from the International Bureau of WIPO, Geneva, Switzerland, 9 pages.

English-Language Abstract for JP 2001-343324 A, published Dec. 14, 2001; 1 page.

Non-Final Rejection mailed Sep. 9, 2013 for U.S. Appl. No. 12/989,902, filed Jan. 5, 2011; 12 pages.

Final Rejection mailed Mar. 19, 2014 for U.S. Appl. No. 12/989,902, filed Jan. 5, 2011; 16 pages.

Notice of Allowance mailed Oct. 1, 2014 for U.S. Appl. No. 12/989,902, filed Jan. 5, 2011; 9 pages.

Notice of Allowance mailed Nov. 5, 2014 for U.S. Appl. No. 12/989,902, filed Jan. 5, 2011; 9 pages.

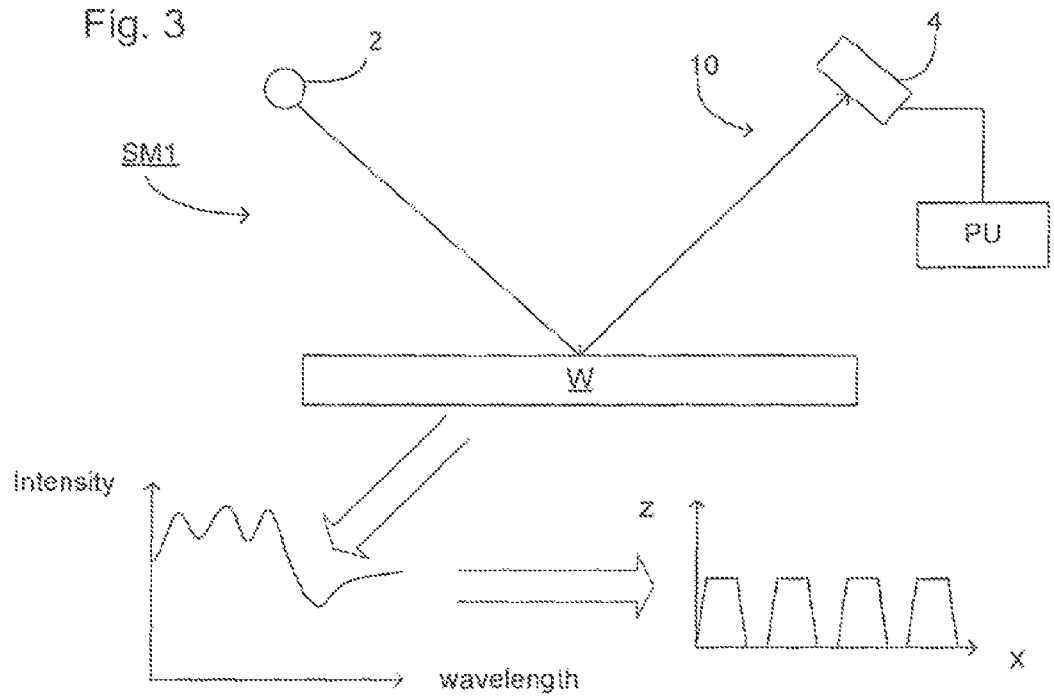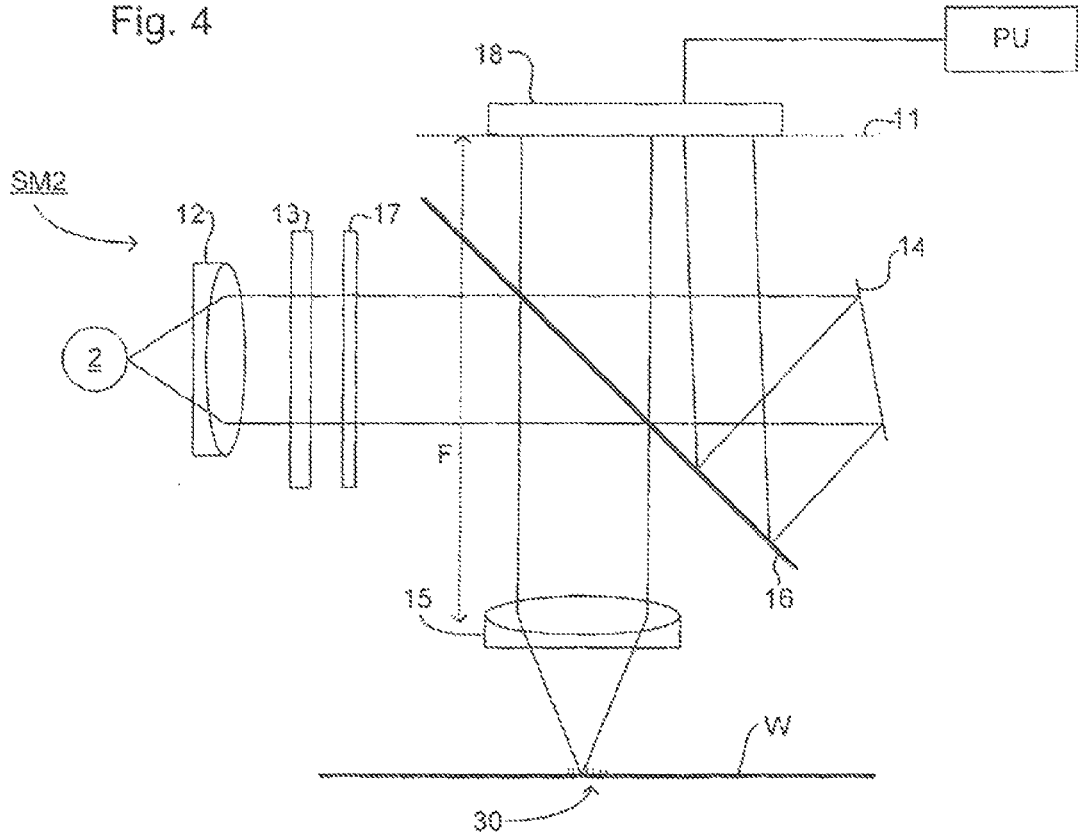

US 9,280,065 B2

INSPECTION APPARATUS TO DETECT A TARGET LOCATED WITHIN A PATTERN FOR LITHOGRAPHY

This application is related to U.S. application Ser. No. 12/989,902, filed Jan. 5, 2011, PCT App. PCT/EP2009/003051 filed on Apr. 27, 2009, and U.S. Prov. Appl. No. 61/071,673, filed on May 12, 2008, which are all incorporated by reference herein in their entireties.

FIELD

The present invention relates to methods of inspection usable, for example, in the manufacture of devices by lithographic techniques and to methods of manufacturing devices using lithographic techniques.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g. including part of, one, or several dies) on a substrate (e.g. a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

In order to monitor the lithographic process, it is desirable to measure parameters of the patterned substrate, for example the overlay error between successive layers formed in or on it. There are various techniques for making measurements of the microscopic structures formed in lithographic processes, including the use of scanning electron microscopes and various specialized tools. One form of specialized inspection tool is a scatterometer in which a beam of radiation is directed onto a target on the surface of the substrate and properties of the scattered or reflected beam are measured. By comparing the properties of the beam before and after it has been reflected or scattered by the substrate, the properties of the substrate can be determined. This can be done, for example, by comparing the reflected beam with data stored in a library of known measurements associated with known substrate properties. Two main types of scatterometer are known. Spectroscopic scatterometers direct a broadband radiation beam onto the substrate and measure the spectrum (intensity as a function of wavelength) of the radiation scattered into a particular narrow angular range. Angularly resolved scatterometers use a monochromatic radiation beam and measure the intensity of the scattered radiation as a function of angle.

In scatterometers and lithographic apparatus, targets are used in the determination of overlay errors. These are conventionally positioned in the scribe lanes between the patterns. The overlay error at the target site is thus measured. However, the overlay error at the position of the pattern is therefore an interpolation between the overlay at different points surrounding the pattern.

Although the targets could be positioned within the patterns themselves, this is not desirable because the targets used are relatively large and therefore take up too much of the area that is designed for product patterns, thereby compromising device functionality.

SUMMARY

It is desirable to provide a method of measuring a target which is sufficiently small to be placed on the substrate within the pattern.

According to an aspect of the invention, there is provided an inspection apparatus, lithographic apparatus or lithographic cell configured to measure a property of a substrate.

According to an aspect of the invention, there is provided a method of measuring a target on a substrate, the method including projecting radiation onto a substrate; detecting the radiation reflected by the substrate and forming a set of fourier transform data based on the detected radiation; removing portions of the fourier transform data which correspond to the target to form reduced fourier transform data; interpolating the portions of the reduced fourier transform data which were removed, to form product fourier transform data; and subtracting the product fourier transform data from the fourier transform data to form target data.

According to an embodiment of the invention, there is provided an inspection apparatus configured to measure a target on a substrate, the apparatus including a radiation projector configured to illuminate the substrate with radiation; a high numerical aperture lens; a detector configured to detect the radiation reflected from a surface of the substrate, the detected radiation being used to form fourier transform data; and a data processor configured to remove portions of the fourier transform data which correspond to the target to form reduced fourier transform data; interpolate the portions of the removed reduced fourier transform data to form product fourier transform data; and subtract the product fourier transform data from the fourier transform data to form target data.

According to an aspect of the invention, there is provided a lithographic apparatus including a projection system configured to project an image of a pattern on to a substrate; and an inspection apparatus configured to measure a target on the substrate, the inspection apparatus including a radiation projector configured to illuminate the substrate with radiation; a high numerical aperture lens; a detector configured to detect the radiation reflected from a surface of the substrate, the detected radiation being used to form fourier transform data; and a data processor configured to remove portions of the fourier transform data which correspond to the target to form reduced fourier transform data; interpolate the portions of the removed reduced fourier transform data to form product fourier transform data; and subtract the product fourier transform data from the fourier transform data to form target data.

According to an aspect of the invention, there is provided a method of measuring a target on a substrate, the substrate including a known pattern and the target, the method including illuminating the substrate with radiation; detecting the radiation reflected by the substrate to form a fourier transform data; performing a fourier transform on the known pattern to form pattern fourier transform data; and subtracting the pattern fourier transform data from the fourier transform data to form target data.

According to an aspect of the invention, there is provided an inspection apparatus configured to measure a target on a substrate, the substrate including a known pattern and the target, the apparatus including a radiation projector configured to illuminate the substrate with radiation; a high numerical aperture lens; a detector configured to detect the radiation reflected from a surface of the substrate, the detected radiation being used to form fourier transform data; and a data processor configured to perform a fourier transform on the known pattern to form pattern fourier transform data; and subtract the product fourier transform data from the fourier transform data to form target data.

According to an aspect of the invention, there is provided an inspection apparatus configured to measure a target on a substrate, the substrate comprising a known pattern and the target, the apparatus including a radiation projector configured to illuminate the substrate with radiation; a high numerical aperture lens; a detector configured to detect the radiation reflected from a surface of the substrate, the detected radiation being used to form fourier transform data; and a data processor configured to perform a fourier transform on the known pattern to form pattern fourier transform data; and subtract the product fourier transform data from the fourier transform data to form target data.

According to an aspect of the invention, there is provided a lithographic apparatus including a projection system configured to project an image of a pattern on to a substrate; and an inspection apparatus configured to measure a target on the substrate, the substrate comprising a known pattern and the target, the inspection apparatus including a radiation projector configured to illuminate the substrate with radiation; a high numerical aperture lens; a detector configured to detect the radiation reflected from a surface of the substrate, the detected radiation being used to form fourier transform data; and a data processor configured to perform a fourier transform on the known pattern to form pattern fourier transform data; and subtract the pattern fourier transform data from the fourier transform data to form target data.

According to an aspect of the invention, there is provided a method for determining a symmetry of conformal coatings on a substrate comprising a sacrificial feature, the method including applying a conformal coating to a substrate comprising the sacrificial feature; etching the conformal coating to reveal the feature; removing the feature to leave a conformal feature; illuminating the substrate with radiation; detecting the radiation reflected by the substrate to form reflected radiation data; performing a fourier transform on the reflected radiation data to form fourier transform data; removing portions of the fourier transform data which correspond to the conformal feature to form reduced fourier transform data; interpolating the portions of the removed reduced fourier transform data which to form product fourier transform data; and subtracting the product fourier transform data from the fourier transform data to form target data.

According to an aspect of the invention, there is provided a method for determining a symmetry of conformal coatings on a substrate including a known pattern and a sacrificial feature, the method including applying a conformal coating to the substrate comprising the sacrificial feature; etching the conformal coating to reveal the feature; removing the feature to leave a conformal feature; illuminating the substrate with radiation; detecting the radiation reflected by the substrate, the reflected radiation being used to form a set of fourier transform data; performing a fourier transform on the known pattern to form pattern fourier transform data; and subtracting the pattern fourier transform data from the fourier transform data to form target data.

BRIEF DESCRIPTION OF THE DRAWINGS

Embodiments of the invention will now be described, by way of example only, with reference to the accompanying schematic drawings in which corresponding reference symbols indicate corresponding parts, and in which:

FIG. 3 depicts a scatterometer in accordance with an embodiment of the invention;

FIG. 4 depicts a scatterometer in accordance with an embodiment of the invention;

DETAILED DESCRIPTION

Figure 1:
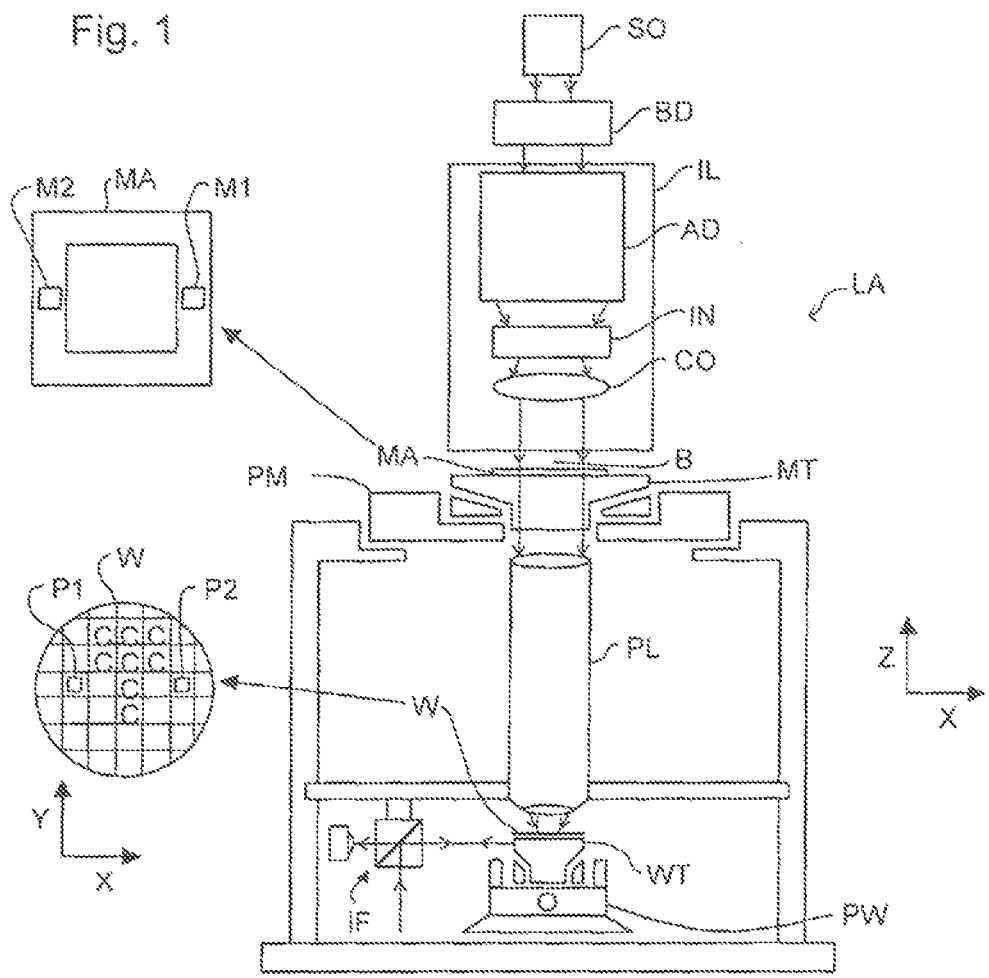
FIG. 1 depicts a lithographic apparatus in accordance with an embodiment of the invention.

FIG. 1 schematically depicts a lithographic apparatus. The apparatus includes an illumination system (illuminator) IL configured to condition a radiation beam B (e.g. UV radiation or DUV radiation); a patterning device support or support structure (e.g. a mask table) MT constructed to support a patterning device (e.g. a mask) MA and connected to a first positioner PM configured to accurately position the patterning device in accordance with certain parameters; a substrate table or support (e.g. a wafer table) WT constructed to hold a substrate (e.g. a resist-coated wafer) W and connected to a second positioner PW configured to accurately position the substrate in accordance with certain parameters; and a projection system (e.g. a refractive projection lens system) PL configured to project a pattern imparted to the radiation beam B by patterning device MA onto a target portion C (e.g. including one or more dies) of the substrate W.

The illumination system may include various types of optical components, such as refractive, reflective, magnetic, electromagnetic, electrostatic or other types of optical components, or any combination thereof, to direct, shape, or control radiation.

The patterning device support holds the patterning device in a manner that depends on the orientation of the patterning device, the design of the lithographic apparatus, and other conditions, such as for example whether or not the patterning device is held in a vacuum environment. The patterning device support can use mechanical, vacuum, electrostatic or other clamping techniques to hold the patterning device. The patterning device support may be a frame or a table, for example, which may be fixed or movable as required. The patterning device support may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g. employing a transmissive mask). Alternatively, the apparatus may be of a reflective type (e.g. employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g. water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD including, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may include an adjuster AD to adjust the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may include various other components, such as an integrator IN and a condenser CO. The illuminator may be used to condition the radiation beam, to have a desired uniformity and intensity distribution in its cross-section.

The radiation beam B is incident on the patterning device (e.g., mask) MA, which is held on the patterning device support (e.g., mask table) MT, and is patterned by the patterning device. Having traversed the patterning device (e.g. mask) MA, the radiation beam B passes through the projection system PL, which focuses the beam onto a target portion C of the substrate W. With the aid of the second positioner PW and position sensor IF (e.g. an interferometric device, linear encoder, 2-D encoder or capacitive sensor), the substrate table WT can be moved accurately, e.g. so as to position different target portions C in the path of the radiation beam B. Similarly, the first positioner PM and another position sensor (which is not explicitly depicted in FIG. 1) can be used to accurately position the patterning device (e.g. mask) MA with respect to the path of the radiation beam B, e.g. after mechanical retrieval from a mask library, or during a scan. In general, movement of the patterning device support (e.g. mask table) MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the patterning device support (e.g. mask table) MT may be connected to a short-stroke actuator only, or may be fixed. Patterning device (e.g. mask) MA and substrate W may be aligned using patterning device alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device (e.g. mask) MA, the patterning device alignment marks may be located between the dies.

The depicted apparatus could be used in at least one of the following modes:

1. In step mode, the patterning device support (e.g. mask table) MT and the substrate table WT are kept essentially stationary, while an entire pattern imparted to the radiation beam is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the patterning device support (e.g. mask table) MT and the substrate table WT are scanned synchronously while a pattern imparted to the radiation beam is projected onto a target portion C (i.e. a single dynamic exposure). The velocity and direction of the substrate table WT relative to the patterning device support (e.g. mask table) MT may be determined by the (de-)magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion.

3. In another mode, the patterning device support (e.g. mask table) MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
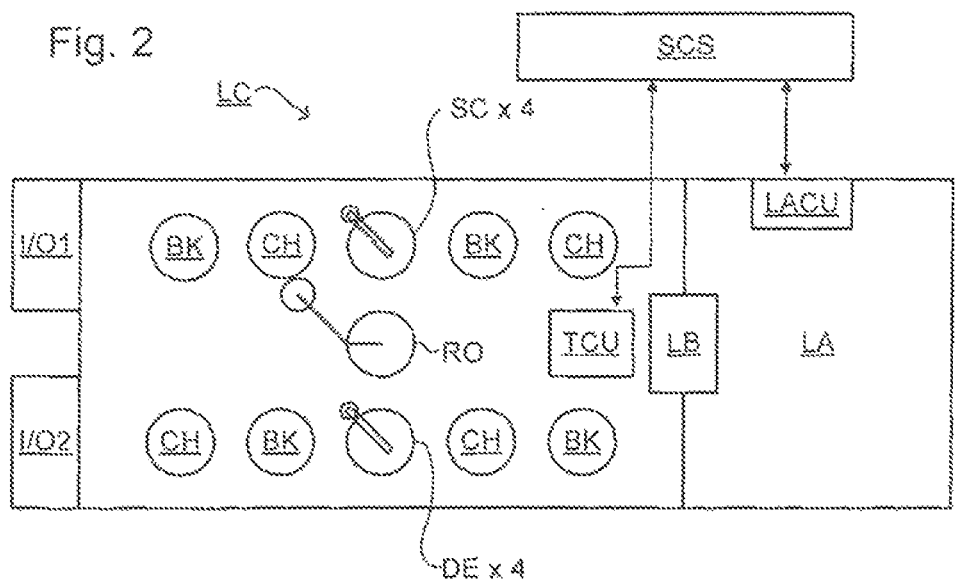
FIG. 2 depicts a lithographic cell or cluster in accordance with an embodiment of the invention.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. If errors are detected, adjustments may be made to exposures of subsequent substrates, especially if the inspection can be done soon and fast enough that other substrates of the same batch are still to be exposed. Also, already exposed substrates may be stripped and reworked—to improve yield—or discarded—thereby avoiding performing exposures on substrates that are known to be faulty. In a case where only some target portions of a substrate are faulty, further exposures can be performed only on those target portions which are good.

An inspection apparatus is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To enable most rapid measurements, it is desirable that the inspection apparatus measure properties in the exposed resist layer immediately after the exposure. However, the latent image in the resist has a very low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB) which is customarily the first step carried out on exposed substrates and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of faulty substrates but may still provide useful information.

FIG. 3 depicts a scatterometer SM1 which may be used in an embodiment of the present invention. It includes a broadband (white light) radiation projector 2 which projects radiation onto a substrate W. The reflected radiation is passed to a spectrometer detector 4, which measures a spectrum 10 (intensity as a function of wavelength) of the specular reflected radiation. From this data, the structure or profile giving rise to the detected spectrum may be reconstructed by processing unit PU, e.g. by Rigorous Coupled Wave Analysis and non-linear regression or by comparison with a library of simulated spectra as shown at the bottom of FIG. 3. In general, for the reconstruction the general form of the structure is known and some parameters are assumed from knowledge of the process by which the structure was made, leaving only a few parameters of the structure to be determined from the scatterometry data. Such a scatterometer may be configured as a normal-incidence scatterometer or an oblique-incidence scatterometer.

Another scatterometer SM2 that may be used with an embodiment of the present invention is shown in FIG. 4. In this device, the radiation emitted by radiation source 2 is focused using lens system 12 through interference filter 13 and polarizer 17, reflected by partially reflected surface 16 and is focused onto substrate W via a microscope objective lens 15, which has a high numerical aperture (NA), preferably at least 0.9 and more preferably at least 0.95. Immersion scatterometers may even have lenses with numerical apertures over 1. The reflected radiation then transmits through partially reflective surface 16 into a detector 18 in order to have the scatter spectrum detected. The detector may be located in the back-projected pupil plane 11, which is at the focal length of the lens system 15, however the pupil plane may instead be re-imaged with auxiliary optics (not shown) onto the detector. The pupil plane is the plane in which the radial position of radiation defines the angle of incidence and the angular position defines azimuth angle of the radiation. The detector is preferably a two-dimensional detector so that a two-dimensional angular scatter spectrum of a substrate target 30 can be measured. The detector 18 may be, for example, an array of CCD or CMOS sensors, and may use an integration time of, for example, 40 milliseconds per frame.

A reference beam is often used for example to measure the intensity of the incident radiation. To do this, when the radiation beam is incident on the beam splitter 16 part of it is transmitted through the beam splitter as a reference beam towards a reference mirror 14. The reference beam is then projected onto a different part of the same detector 18.

A set of interference filters 13 is available to select a wavelength of interest in the range of, say, 405-790 nm or even lower, such as 200-300 nm. The interference filter may be tunable rather than including a set of different filters. A grating could be used instead of interference filters.

The detector 18 may measure the intensity of scattered light at a single wavelength (or narrow wavelength range), the intensity separately at multiple wavelengths or integrated over a wavelength range. Furthermore, the detector may separately measure the intensity of transverse magnetic- and transverse electric-polarized light and/or the phase difference between the transverse magnetic- and transverse electric-polarized light.

Using a broadband light source (i.e. one with a wide range of light frequencies or wavelengths—and therefore of colors) is possible, which gives a large etendue, allowing the mixing of multiple wavelengths. The plurality of wavelengths in the broadband preferably each has a bandwidth of $\delta\lambda$ and a spacing of at least 2 $\delta\lambda$ (i.e. twice the bandwidth). Several "sources" of radiation can be different portions of an extended radiation source which have been split using fiber bundles. In this way, angle resolved scatter spectra can be measured at multiple wavelengths in parallel. A 3-D spectrum (wavelength and two different angles) can be measured, which contains more information than a 2-D spectrum. This allows more information to be measured which increases metrology process robustness. This is described in more detail in EP1,628,164A.

The target 30 on substrate W may be a grating, which is printed such that after development, the bars are formed of solid resist lines. The bars may alternatively be etched into the substrate. This pattern is sensitive to chromatic aberrations in the lithographic projection apparatus, particularly the projection system PL, and illumination symmetry and the presence of such aberrations will manifest themselves in a variation in the printed grating. Accordingly, the scatterometry data of the printed gratings is used to reconstruct the gratings. The parameters of the grating, such as line widths and shapes, may be input to the reconstruction process, performed by processing unit PU, from knowledge of the printing step and/or other scatterometry processes.

An embodiment of the invention allows smaller targets to be more accurately measured. Thus targets used in conjunction with an embodiment of the invention may be approximately 10 μm×10 μm. When the radiation is focused on the target, there will additionally be diffraction from the surrounding pattern. In an embodiment of the invention, the diffraction from the surrounding pattern (in the pupil plane) is filtered out such that only the portions from the target remain.

Figure 5:
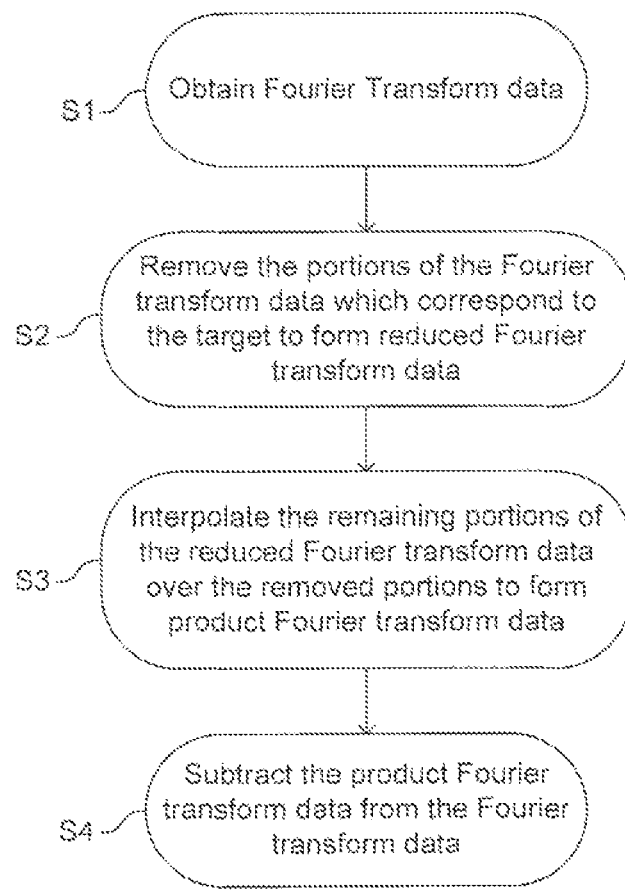
FIG. 5 is a flow diagram in accordance with an embodiment of the invention.

An embodiment of the invention operates in the pupil plane and includes the following procedures, as shown in FIG. 5:
  a) obtaining fourier transform data, S1;
  b) removing portions of the Fourier transform corresponding to the target, S2;
  c) interpolating the remaining fourier transform over the removed portions, S3; and
  d) subtracting the fourier transform of procedure (c) from the fourier transform of procedure (a), S4.

Procedure (a) may be achieved by placing the detector in the pupil plane (or alternatively by detecting data and performing a fourier transform). Then, based on the aperture, pitch and orientation of the target the portions of the fourier transform data corresponding to the target can be removed. The procedure of obtaining transform data and removing portions of the Fourier transform may be carried out by a calculator provided in the scatterometer SM1 or SM2. The targets generally have a pitch of about 500-1000 nm, whereas the surrounding pattern has a much smaller pitch. Thus, if radiation of a suitable wavelength is used and combined with a suitable numerical aperture there will first order contributions only from the target. There may additionally be some lower intensity scattering from the surrounding patterns, which procedure (c) is intended to estimate. Any knowledge of the surrounding pattern may be used to improve the interpolation of procedure (c). Procedure (c) estimates the cross talk from the surrounding pattern. By subtracting the fourier transform of the surrounding pattern (including estimated cross talk) from the original fourier transform data the fourier transform of the target remains. The target data remaining may then be used to calculate the overlay error, or for any other purposes. The procedures a-d, or part thereof, may be carried out with the use of a data processor.

Figure 6:
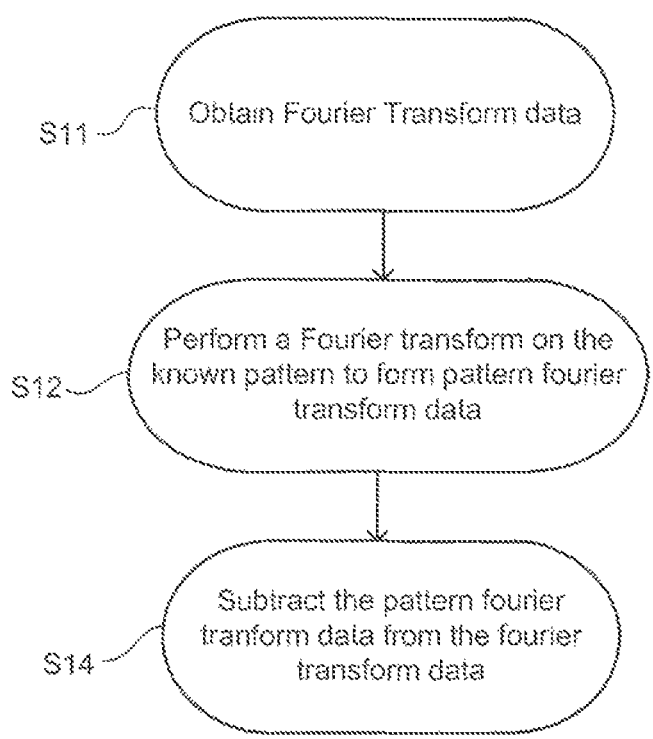
FIG. 6 is a flow diagram in accordance with an embodiment of the invention.

In another embodiment of the invention the fourier transform of the pattern (excluding the target) on the substrate is known. An embodiment of the invention includes the following procedures, as shown in FIG. 6:
  (a) obtaining fourier transform data, S11;
  (b) performing a fourier transform on the known pattern, S12; and
  (c) subtracting the fourier transform of procedure (b) from the fourier transform of procedure (a), S14.

This method avoids the need for approximating the cross talk from the pattern and the lower intensity scattering by using the fourier transform of the known pattern. Thus, in this embodiment a larger angular spread may be used and a target with a larger overlay range may be detected. However, this method relies on the structure of the surrounding pattern being known.

Figure 7A:
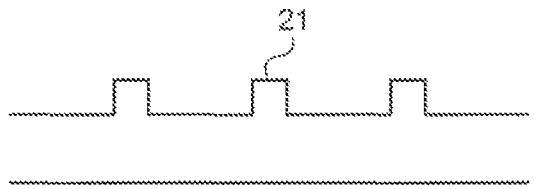
FIGS. 7a-d depict some of the procedures involved in an embodiment of the invention.
Figure 7B:
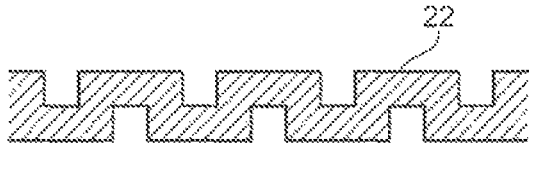
Figure 7C:
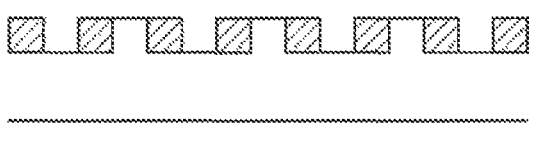
Figure 7D:
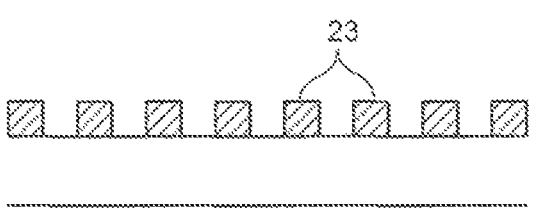

According to a further embodiment of the invention, the method is used to determine the symmetry of conformal coatings. According to this embodiment, a sacrificial feature 21 is generated, as shown in FIG. 7a and as shown in FIG. 7b a coating 22 is applied. The conformal coating is etched back to reveal the top of the feature (FIG. 7c). The feature is then removed, usually by etching to leave just the conformal layer feature, 23 (FIG. 7d) at a lower pitch than the original feature. Radiation is then projected onto the substrate and the reflected radiation detected. The method then includes the following procedures:
  a) obtaining fourier transform data (from the reflected radiation data);
  b) removing portions of the Fourier transform corresponding to the conformal layer feature;
  c) interpolating the remaining fourier transform over the removed portions; and
  d) subtracting the fourier transform of procedure (c) from the fourier transform of procedure (a).

The resulting data can then be used to determine characteristics of the coating and the substrate itself.

Alternatively, if the surrounding pattern is known, the method may include procedures in accordance with the second embodiment of the invention, namely:
  (a) obtaining fourier transform data;
  (b) performing a fourier transform on the known pattern; and
  (c) subtracting the fourier transform of procedure (b) from the fourier transform of procedure (a).

An embodiment of the invention has been described primarily in conjunction with an angle resolved scatterometer, although it may also be used in conjunction with, for example, a spectroscopic scatterometer or an ellipsometer.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g. having a wavelength of or about 365, 355, 248, 193, 157 or 126 nm) and extreme ultra-violet (EUV) radiation (e.g. having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g. semiconductor memory, magnetic or optical disk) having such a computer program stored therein.

The descriptions above are intended to be illustrative, not limiting. Thus, it will be apparent to one skilled in the art that modifications may be made to the invention as described without departing from the scope of the claims set out below.

The invention claimed is:

1. A method of measuring a target on a substrate, wherein the target is located within a surrounding pattern on the substrate, the method comprising:
    illuminating the target and the surrounding pattern with radiation;
    detecting the radiation reflected by the target and the surrounding pattern and forming a first set of data based on the detected radiation;
    removing portions of the first set of data which correspond to the target to form reduced data;
    interpolating the remaining portions of the reduced data over the removed portions to form product data; and
    subtracting the product data from the first set of data to form target data.

2. The method according to claim 1, wherein the detecting comprises detecting the radiation in the pupil plane.

3. The method according to claim 1, wherein the detecting comprises performing a Fourier transform on reflected radiation data to form the first set of data.

4. The method according to claim 1, further comprising analyzing the target data to determine an overlay error, or a critical dimension or a shape of a feature, or any combination of the foregoing.

5. An inspection apparatus comprising:
    a radiation projector configured to illuminate a target and a pattern surrounding the target on a substrate with radiation;
    a detector configured to detect the radiation reflected from the target and the pattern surrounding the target, the detected radiation being used to form a first set of data; and
    a processor configured to:
        remove portions of the first set of data which correspond to the target to form reduced data;
        interpolate the remaining portions of the reduced data over the removed portions to form product data; and
        subtract the product data from the first set of data to form target data.

6. The inspection apparatus according to claim 5, wherein the inspection apparatus comprises an angle resolved scatterometer.

7. The inspection apparatus according to claim 5, wherein the inspection apparatus comprises an ellipsometer.

8. A lithographic apparatus comprising:
    a projection system configured to project an image of a pattern on to a substrate; and
    an inspection apparatus configured to measure a target on the substrate, wherein the target is located within a surrounding pattern on the substrate, the inspection apparatus comprising:
        a radiation projector configured to illuminate the target and the surrounding pattern with radiation;
        a detector configured to detect the radiation reflected from the target and the surrounding pattern, the detected radiation being used to form a first set of data; and
        a processor configured to:
            remove portions of the first set of data which correspond to the target to form reduced data;
            interpolate the remaining portions of the reduced data over the removed portions to form product data; and
            subtract the product data from the first set of data to form target data.

9. A data processor configured to process a first set of data to measure a target on a substrate, wherein the target is located within a surrounding pattern on the substrate, the data processor being configured to:
    remove portions of the first set of data which correspond to the target to form reduced data;
    interpolate the remaining portions of the reduced data over the removed portions to form product data; and
    subtract the product data from the first set of data to form target data;
    determine one or more parameters of the target from the target data; and
    reconstruct the target using at least the one or more parameters.

10. A method of measuring a target on a substrate, the substrate comprising a pattern and the target, the method comprising:
    illuminating the pattern and the target with radiation;
    detecting the radiation reflected by the pattern and the target;
    performing a first Fourier transform on the detected radiation to form Fourier transform data;
    performing a second Fourier transform on the known pattern to form pattern Fourier transform data; and
    subtracting the pattern Fourier transform data from the Fourier transform data to form target data.

11. The method according to claim 10, further comprising analyzing the target data to determine an overlay error, or a critical dimension or a shape of a feature, or any combination of the foregoing.

12. An inspection apparatus configured to measure a target on a substrate, the substrate comprising a pattern and the target, the apparatus comprising:
    a radiation projector configured to illuminate the pattern and the target with radiation;
    a detector configured to detect the radiation reflected from the known pattern and the target; and
    a processor configured to
        perform a first Fourier transform on the detected radiation to form Fourier transform data,
        perform a second Fourier transform on the known pattern to form pattern Fourier transform data, and
        subtract the pattern Fourier transform data from the Fourier transform data to form target data.

13. The inspection apparatus according to claim 12, wherein the inspection apparatus comprises an angle resolved scatterometer.

14. The inspection apparatus according to claim 12, wherein the inspection apparatus comprises an ellipsometer.

15. A lithographic apparatus comprising:
a projection system configured to project an image of a pattern on to a substrate; and
an inspection apparatus configured to measure a target on the substrate, the substrate comprising a pattern and the target, the inspection apparatus comprising:
a radiation projector configured to illuminate the pattern and the target with radiation;
a detector configured to detect the radiation reflected from the pattern and the target; and
a data processor configured to:
perform a first Fourier transform on the detected radiation to form Fourier transform data,
perform a second Fourier transform on the pattern to form pattern Fourier transform data, and
subtract the pattern Fourier transform data from the Fourier transform data to form target data.

16. A processor configured to process Fourier transform data to measure a target on a substrate, the substrate comprising a pattern and the target, the processor being configured to:
perform a first Fourier transform on detected radiation from the pattern and the target to form Fourier transform data;
perform a second Fourier transform on the pattern to form pattern Fourier transform data; and
subtract the pattern Fourier transform data from the Fourier transform data to form target data
determine one or more parameters of the target from the target data; and
reconstruct the target using at least the one or more parameters.

17. A method for determining a symmetry of conformal coatings on a substrate comprising a sacrificial feature, the method comprising:
applying a conformal coating to a substrate comprising the sacrificial feature;
etching the conformal coating to reveal the feature;
removing the feature to leave a conformal feature;
illuminating the substrate with radiation;
detecting the radiation reflected by the substrate to form reflected radiation data;
removing portions of the reflected radiation data which correspond to the conformal feature to form reduced data;
interpolating the remaining portions of the reduced data over the removed portions to form product data; and
subtracting the product data from the reflected radiation data to form target data.

18. The method according to claim 17, further comprising forming the sacrificial feature on the substrate.

* * * * *

UNITED STATES PATENT AND TRADEMARK OFFICE
CERTIFICATE OF CORRECTION

PATENT NO. : 9,280,065 B2  
APPLICATION NO. : 14/664007  
DATED : March 8, 2016  
INVENTOR(S) : Marcus Adrianus Van De Kerkhof It is certified that error appears in the above-identified patent and that said Letters Patent is hereby corrected as shown below:

On the Title Page

Above the application number (item 21), please insert --This patent is subject to a terminal disclaimer.--.

Item (45) after "Date of Patent:", please insert --*--.

Signed and Sealed this
Fifth Day of July, 2016

Michelle K. Lee
*Director of the United States Patent and Trademark Office*